United States Patent [19]
Eberendu et al.

[11] Patent Number: 5,512,488
[45] Date of Patent: Apr. 30, 1996

[54] COLORIMETRIC ASSAY FOR BIOACTIVE POLYSACCHARIDE

[75] Inventors: Alexis N. R. Eberendu, Carrollton; Bill H. McAnalley, Grand Prairie, both of Tex.

[73] Assignee: Carrington Laboratories, Inc., Irving, Tex.

[21] Appl. No.: 238,377

[22] Filed: May 5, 1994

[51] Int. Cl.$^6$ .................................................. G01N 33/00
[52] U.S. Cl. .............................. 436/94; 436/169; 435/4; 435/31; 435/101
[58] Field of Search ........................ 436/94, 164, 165, 436/169; 435/101, 4, 31, 32; 422/56

[56] References Cited

U.S. PATENT DOCUMENTS

| | | | |
|---|---|---|---|
| 3,306,827 | 2/1967 | Craig | 435/32 |
| 3,941,658 | 3/1976 | Lameris et al. | 435/32 |
| 4,207,200 | 6/1980 | Muller et al. | 252/184 |
| 4,225,669 | 9/1980 | Melnick et al. | 435/29 |
| 4,385,046 | 5/1983 | Milbrath et al. | 424/1 |
| 4,544,546 | 10/1985 | Wang et al. | 424/7.1 |
| 4,568,637 | 2/1986 | Klein | 435/18 |
| 5,173,434 | 12/1992 | Morris et al. | 436/172 |
| 5,310,646 | 5/1994 | Whitley | 435/4 |
| 5,334,502 | 8/1994 | Sangha | 435/7.2 |

OTHER PUBLICATIONS

*Gann*, 67, Takuma Sasaki, et al., "Antitumor Activity of Degraded Products of Lentinan: Its Correlation With Molecular Weight", pp. 191–195, (Apr. 1976).

*Carbohydrate Research*, 29, Kozo Ogawa, et al., "The Dependence of the Conformation of a (1→3)–β–D–Glucan On Chain–Length in Alkaline Solution", pp. 397–403, (1973).

*Primary Examiner*—Timothy M. McMahon
*Assistant Examiner*—N. Bhat
*Attorney, Agent, or Firm*—Hitt Chwang & Gaines

[57] ABSTRACT

An assay for the qualitative and quantitative determination of a bioactive polysaccharide, such as acemannan, in a product, such as an aloe vera-containing product. The method uses a complexing agent to react with the bioactive polysaccharide present, if any, in the product to give a color change. The detected color change is compared with standard color changes generated by reacting the complexing agent with different known amounts of the bioactive polysaccharide, wherein differences between the color changes compared are dependent upon the presence or amount of the bioactive polysaccharide in the product. The assay can be confirmed by detecting a second color change of a different aliquot of the product with a different complexing agent.

39 Claims, 9 Drawing Sheets

COLORIMETRIC ASSAY FOR BIOACTIVE POLYSACCHARIDE

BACKGROUND

The present invention relates to a colorimetric assay method, apparatus and kit for the qualitative and quantitative determination of a bioactive polysaccharide in a product, more specifically, for the qualitative and quantitative determination of acemannan in an aloe-containing product.

Aloe is a tropical or subtropical plant characterized by lance-shaped leaves with jagged edges and sharp points. For centuries, this plant has been considered to have, and has been used for its, medicinal and therapeutic properties without any clear understanding or scientific analysis of the bases for such properties.

Because of the lack of knowledge about the aloe plant and its characteristics, most methods employed for the processing of the plant and its components result in end products which do not consistently contain the active ingredients. Traditional processes for the production of various aloe products typically involve crushing (pressure rollers, grinding e.g. use of a Thompson aloe leaf slitter), or pressing (TCS pressure extruder) of the entire leaf of the aloe plant to produce an aloe vera juice, followed by various steps of filtration and stabilization of the juice. The resulting solution is then incorporated in, or mixed with, other solutions or agents to produce the products which could be, for example, a cosmetic, a health food drink, or a topical ointment. Unfortunately, because of improper processing procedures, many of these so-called aloe products contain no active ingredients, namely, mucilaginous polysaccharides ("MP").

The principal disadvantage of such state of the art processes is the failure to recognize, and to take into account, that different components of the aloe leaf have characteristics that may not only be inconsistent with the intended use of the final product, but in many instances were deleterious to such use. Further, unless carefully controlled processes are used in processing the leaves of the aloe plant, the active ingredients, namely mucilaginous polysaccharides, of the leaves are destroyed during the process.

These active ingredients, the polysaccharides, have been identified, isolated and stabilized as described in U.S. Pat. Nos. 4,957,907 and 4,959,214, incorporated herein by reference. These active polysaccharides are hereinafter referred to as acemannan. Acemannan is an ordered linear polymer of substantially acetylated mannose monomers.

The fresh unpreserved gel is about 98.5–99.2% water. The total solid that remains after the water has been removed ranges from 0.8 to 1.5% of the total weight. The major constituents of that solid are mucilage, fiber, monosaccharides, polysaccharides, proteins, ash, fats, aloin and resin.

The physiological activity of acemannan and its pharmaceutical applications have been the object of numerous research studies at a number of laboratories, including Carrington Laboratories. These studies have primarily focused on the action of the activity of acemannan as an antiviral agent, an immunomodulator, a means of reducing opportunistic infections, and as a means of stimulating the healing processes.

Acemannan has been shown in laboratory studies to increase up to 300% in 48 hours the replication of fibroblasts in tissue culture which are known to be responsible for healing burns, ulcers and other wounds of the skin and of the gastrointestinal lining.

Acemannan has also been shown to increase DNA synthesis in the nucleus of fibroblasts. The increase in DNA synthesis in turn increases the rate of metabolic activity and cell replication which are fundamental steps in the healing process.

Acemannan has been shown in controlled studies to increase the rate of healing in animals as well, such as an effective treatment for gastric ulcers in animal studies. Over a three year period, laboratory rats, the stomachs of which react similarly to that of humans, were tested. Acemannan was found to be equivalent to or superior to current medications used for the treatment of gastric ulcers. Most such products act to inhibit hydrochloric acid in the stomach. Acemannan, however, works on a different principle and does not alter the natural flow of digestive acids. More recently, drinks containing extract of aloe vera plant have been placed on the market for consumers.

Several biochemical, inorganic and trace metal constituents have been associated with the plant extract. Prior to, and even after the discovery of active polysaccharides in aloe, various of these inorganic constituents have been claimed to be responsible for the "healing" power of the plant. As a result, manufacturers "process" the Aloe vera plant in different ways to suit their own beliefs and understanding. Thus, the scientific literature contains many contradictory opinions as to what components in the aloe vera plant are responsible for these "healing" effects. These contradictions have led to various methods of processing the aloe vera plant and to difficulty in establishing a reliable and easy to use composition standard for aloe vera plant and products. In some cases, the process used to process the aloe vera removes all of the polysaccharides and most of the other organic components of the plant, a process which causes the product to loose its biological activities, its characteristic aloe taste and its natural aloe texture. In such instances, the manufacturers try to reform the aloe texture by adding flavoring agents and non-aloe polysaccharides such as maltodextrin, dextran, plant gums, dextrose, etc. to the products. Unfortunately, however, these adulterated products can still be certified as "aloe vera products," whether or not they contain the acemannan.

Because of the large number in the market of these adulterated products with no acemannan, several attempts have been made over the years to develop a standard assay to measure the presence of active ingredients, such as acemannan, present in the aloe products. A comprehensive effort at developing a chemical component profile of aloe was made by the International Aloe Science Council (IASC) in 1982–1984. Some thirty parameters were considered relative to the verification of authentic aloe vera products. Out of these more than thirty parameters, four tests were commonly used. These four include percent of total solids, calcium, magnesium and high performance liquid chromatography (HPLC) peak ratios. The recommended standard, however, has inherent problems because three of the four tests, namely, total solid, calcium and magnesium can be found at varying levels in extracts of many other plants and fruits. The fourth test, "HPLC ratio" surprisingly is based on the presence of barbaloin, an anthraquinone derivative found in Aloe sap. Since aloe drink, which is meant for human consumption, is supposed to be substantially free of anthraquinones, the use of the HPLC ratio as a verification means of active ingredients of aloe in a drink containing aloe extract is inappropriate.

Another study to find an acceptable standard for the active ingredient of aloe vera has been conducted at Texas A&M University. Preliminary results of that study have been published in the *SÖFW— Journal,* 119, 255–268 (1993). Apart from the measurement of total solids, magnesium, calcium, potassium and sodium, an "HPLC profile" of aloe extract was obtained using an amino bonded column and a phosphate buffered acetonitrile as the eluant. The publication gives detailed information about an HPLC Profile peak known as "E-Peak." The "E-Peak" is not yet structurally characterized and has not been identified as possessing any bioactivity. Moreover, the HPLC retention time is highly variable and poses analytical problems with aloe drinks which may contain additives and preservatives.

Another assay method to measure polysaccharides of aloe vera involves the steps of initially precipitating the active polysaccharides with alcohol to get rid of alcohol soluble complexes of organic acids, inorganic salts and others. The precipitated polysaccharide is then measured by Dubois assay for total hexose. This assay is also problematic because most polysaccharides such as guar gum, dextran, dextrin, locust bean gum, and others would precipitate in alcohol as well as react positively with Dubois assay for hexose. Thus, products that have been adulterated with these non-aloe polysaccharides could still be certified as products containing the active ingredients of aloe vera.

Yet another assay method that is used is the HPLC Size Exclusion Chromatography (SEC). This is an "in-house" quality control procedure that is effective in determining the quality of the aloe vera product where no attempt to defraud has been made. However, it is difficult to use this procedure to regulate commercial products containing aloe vera.

Therefore, it is seen that there is a need for a reliable, sensitive, simple, specific and relatively foolproof validating assay methodology, apparatus and kit for determining the presence, and the amount, of naturally occurring bioactive polysaccharides found in aloe vera. The present invention is directed to such a methodology, apparatus, and kit.

Congo Red is an indicator primarily used for estimating free mineral acids and also for staining biological samples. Light absorption maximum of Congo Red in 1% w/v aqueous solution is approximately 488 nanometers wavelength. While studying the antitumor activity of Lentinan, a glucan from Lentinus Edodes, Sasaki et al., *Gann,* 67, 191–195 (1976), observed that the absorption maximum of Congo Red shifted toward longer wavelength in the presence of a large molecular weight lentinan polysaccharide. Small molecular weight fractions of the lentinan did not cause a shift in the absorption wavelength. Ogawa et al., *Carbohydrate Research,* 29, 397–403 (1973), reported the formation of a complex between gel-forming D-glucans and Congo Red in alkaline solutions. They postulated that complex formation of polysaccharide with Congo Red was due to orderly conformation of the molecule. However, there was no attempt to investigate whether complex formation was solely dependent on molecular size or whether other micromolecular characteristics of the polysaccharides were more important. Moreover, there was no report of non-glucan polysaccharides demonstrating shift in absorption with Congo Red. Most importantly, there was no attempt to use the Congo Red interaction with the polysaccharides to quantify these bioactive polysaccharides.

SUMMARY

According to one feature of the present invention, there is provided a method for assaying, such as qualitative and quantitative determination of, a bioactive polysaccharide in a product. The method comprises the steps of: Bringing into contact an aliquot of the product with a complexing agent in a suitable medium to form a reaction mixture; allowing color change to occur in the reaction mixture; detecting the color change in the reaction mixture; and comparing the detected color change with standard color changes generated by reacting the complexing agent with different known amounts of the bioactive polysaccharide, wherein differences between the color changes compared are dependent upon the presence or amount of the bioactive polysaccharide in the product sample.

According to another feature of the present invention, there is provided a method of determining and confirming the presence or amount of bioactive polysaccharide in a product. The method comprises the steps of: Bringing into contact a first aliquot of the product with a first complexing agent in a first suitable aqueous buffer solution to form a first reaction mixture; allowing a first color change to occur in the first reaction mixture; detecting the first color change in the first reaction mixture; comparing the first detected color change with first standard color changes generated by reacting the first complexing agent with different known amounts of the bioactive polysaccharide, wherein differences between the color changes compared are dependent upon the presence or amount of the bioactive polysaccharide in the product; separately bringing into contact a second aliquot of the product with a second complexing agent in a second suitable medium to form a second reaction mixture; allowing a second color change to occur in the second reaction mixture; detecting the second color change in the second reaction mixture; and comparing the detected second color change with second standard color changes generated by reacting the second complexing agent with different known amounts of the bioactive polysaccharide, wherein differences between the second color changes compared are dependent upon the presence or amount of the bioactive polysaccharide in the product and wherein the second color change confirms the determination of the presence or amount of the bioactive polysaccharide in the product by the first complexing agent.

According to still another feature of the present invention, there is provided a kit for determining the presence or amount of a bioactive polysaccharide in a product. The kit comprises: A container having calibrated volume markings; a solution of a complexing agent capable of forming color changes with different amounts of the bioactive polysaccharide; and a color reference chart showing different color intensities corresponding to color changes generated by reacting the complexing agent with different known amounts of the bioactive polysaccharide.

According to yet another feature of the present invention, there is provided a kit for determining and confirming the presence or amount of a bioactive polysaccharide in a product. The kit comprises: A container having calibrated volume markings; a first solution of a first complexing agent capable of forming color changes with different amounts of the bioactive polysaccharide; a first color reference chart showing different color intensities corresponding to color changes generated by reacting the first complexing agent with different known amounts of the bioactive polysaccharide; a second solution of a second complexing agent capable of forming color changes with different amounts of the bioactive polysaccharide; and a second color reference chart showing different color intensities corresponding to color changes generated by reacting the second complexing agent with different known amounts of the bioactive polysaccharide.

DETAILED DESCRIPTION

Figure 1:
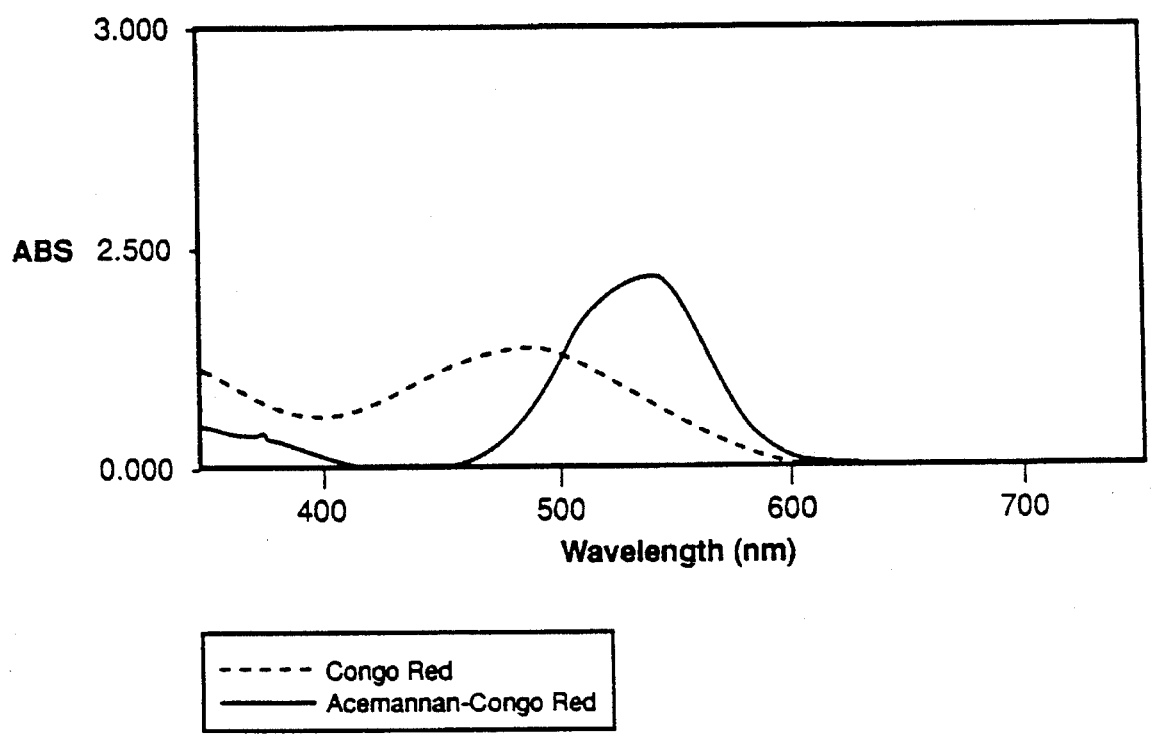
FIG. 1 is a graph showing the absorption of Congo Red and the absorption of the acemannan-Congo Red complex.

The present invention is directed toward a new colorimetric assay method, apparatus and kit specific for the qualitative determination and quantitative estimation of a bioactive polysaccharide, such as acemannan, in a product, such as an aloe vera-containing product. The method is simple, effective and sensitive for quantitatively and qualitatively determining the presence of the bioactive polysaccharides in an aloe vera-containing sample. The apparatus and the kit of the present invention are simple, easy to use and economical to manufacture. The method of the present invention is based on the complex formation between a complexing indicator agent and bioactive polysaccharides, which are immunomodulating. The formation of the complex causes a shift in the absorbance wavelength of the complexing agent which can be read with either a spectrophotometer or a color reference chart device having varying degrees of color intensity. The assay procedure is simple and may be performed in any laboratory equipped with a visible spectrophotometer or a plate reader. The procedure may also be used for on-line monitoring of bioactive polysaccharide production. Additionally, it may be performed by a consumer using a calibrated color reference chart. The applicability of the color reference chart is particularly desirable because it conveniently allows the consumer to determine if the bioactive polysaccharide is present in the product and to estimate the quantity of the active bioactive polysaccharide present. Surprisingly, it has also been found that the color development is negative for many non-aloe polysaccharides such as dextran, guar gums, locust bean gum, maltodextrin, dextrose, other monosaccharides and proteins; hence, the bioactive polysaccharides of interest can be qualitatively and quantitatively determined by the present invention within a specified range.

The present invention also provides a confirmatory colorimetric assay method which utilizes a second complexing indicator agent to form, in a separate assay, a second complex with the bioactive polysaccharides. The formation of the second complex thus confirms the presence and the amount of the bioactive polysaccharides in the sample.

Aloe vera contains two major liquid sources: a yellow latex (exudate) and a clear gel (mucilage). The dried exudate of Aloe barbadensis Miller leaves is referred to as Aloes; the commercial name is Curacao aloe. It is composed mainly of aloin, aloe-emodin and phenols. A number of the phenolics found in the exudate, including anthraquinones and their glycosides, are known to have laxative effect with a reputation as an extremely irritating cathartic.

The mucilaginous jelly from the parenchyma cells of the plant is referred to as Aloe vera gel and contains the bioactive polysaccharides. The jelly is generally produced by peeling away the outer rind of the leaves and homogenizing and filtering the clear gel on the interior of the leaf to remove lignin walled cells, fibers, calcium oxalate, etc. Aloe vera gel is about 98.5–99% water. The solid (0.8–1.5%) is composed of more than 60% polysaccharides such as acemannan. Organic acids/salts and inorganic compounds, especially calcium oxalate, magnesium lactate and amino acids, account for the remainder of the solid.

As used herein, "bioactive" means "possessing biological activity" such as therapeutic activity which denotes the ability to treat a disease. The product can be a drink, a beverage, a skin-care product, a wound-care product, a cosmetic product, a medicinal product or a pharmaceutical product. The product can be in the form of a liquid, a gel, an oil, a foam, a cream, a spray or a solid. "Aliquot," as used herein means a part, a portion, a sample or a fraction of the total. The preferred medium to carry out the assay is a buffered aqueous solution. Other organic solvents, however, may be added to the medium to achieve dissolution of the product.

The present invention shows that a bioactive polysaccharide, such as acemannan from aloe vera, can be determined at parts per million (ppm) level in an aqueous medium, particularly in the ranges of up to about 500 ppm or from about 0.0008% weight/volume (w/v) to about 0.2% w/v. The present invention also shows that the bioactive polysaccharide, such as acemannan, in an aloe vera drink can be detected and quantified after 300-fold dilution in water containing more than 500-fold dextran or dextrose. Interaction of serum proteins with bioactive polysaccharides were also evaluated by this technique.

Commercially, aloe vera is often sold in the form of aloe-vera-containing drink that can be internally consumed. In such instances, the purchaser may desire to know whether the drink still contains the bioactive polysaccharides or the drink has been adulterated and contains no bioactive polysaccharides. With the present invention, a consumer can quickly and accurately determine whether the product has been adulterated and what concentration of the bioactive polysaccharides is present within the ranges of up to about 500 ppm, more preferably, up to about 300 ppm or from about 0.0008% w/v to about 0.2% w/v.

The method of the present invention can also be used to determine the presence or amount of bioactive polysaccharides, particularly of aloe vera, in other products, such as cosmetic products.

As previously mentioned, one method of the present invention employs the use of a complexing agent that complexes with the bioactive polysaccharide to cause a shift in the absorbance wavelength of the complexing agent.

As used herein, a complexing agent is a chemical agent capable of forming coordinate bonds to a molecule or ion of a bioactive polysaccharide to give a complex. The complex may be a positive ion, a negative ion, or a neutral molecule. The complex formed is often colored. Generally, the complexing agent used is an indicator coloring agent which produces a measurable color change when it complexes with a bioactive polysaccharide. Examples of the complexing or indicator agents include: a Naphthyl-amine sulfonate, such as sodium diphenyl-bis-α-naphthyl-amine sulfonate, commercially known as Congo Red, having a molecular formula of $C_{32}H_{22}N_6O_6S_2Na_2$; hexamethylpararosaniline chloride, commercially known as Crystal Violet or Gentian Violet, having a molecular formula of $C_{25}H_{30}ClN_3$; and Toluidine Blue, having the molecular formula of $C_{15}H_{16}N_3SCl$, also known as Basic Blue or tolonium chloride. A preferred indicator agent is Congo Red. The solution of Congo Red is preferably formed from the indicator reagent and water to give a $2\times10^{-4}M$ concentration.

As illustrated by the data reflected in FIG. 1, the peak of the Congo Red agent absorption occurs around 488 nm. However, when Congo Red is complexed with acemannan, the absorption wavelength shifts to around 540 nm. This wavelength shift can be quantitatively and qualitatively read by a spectrophotometer or a plate reader.

A preferred complexing agent, Congo Red, is an indicator coloring agent primarily used for estimating free mineral acids and also for staining biological samples. Light absorption maximum of Congo Red in 1% w/v aqueous solution is approximately 488 nanometers (nm) wavelength. When combined with a bioactive polysaccharide such as acemannan, the maximum absorption shifts to approximately 540 nm wavelength (see FIG. 1). The resulting complex emits a color attributable to that complex that can be read spectrophotometrically by a spectrophotometer or visually by comparing to a color reference chart. Thus, the interaction between the bioactive polysaccharide and the indicator that produced the color change and caused the maximum absorption to shift to a longer wavelength renders this technique a useful method to detect and to quantify bioactive mannans and their derivatives in aqueous matrices.

In one embodiment, an aliquot of the sample to be tested for its content of the bioactive polysaccharide of aloe vera is added to a solution of the indicator to achieve a ratio of about 288 parts to about one part indicator (288:1) and having a pH ranging from about 2 to about 14, preferably in a pH ranging from about 6 to about 14, and more preferably in a pH ranging from about 12 to about 14. More preferably, however, about 500 μL of the sample solution and about 100 μL of $2\times10^{-4}M$ of indicator are added, respectively, with mixing to the aloe product. After the addition of each, the container is swirled until thoroughly mixed. The color change is then observed and read either spectrophotometrically with a spectrophotometer or visually by comparing to a color reference chart.

The apparatus used to read the shift in absorption when the complexing agent interacts with the bioactive polysaccharide may be any conventional spectrophotometer or a calibrated plate reader or color reference chart having graduated varying degrees of color intensity positioned next to a transparent container with a calibrated volume. The varying degrees of color on the color reference chart will be calibrated to the color formed when different concentrations of the bioactive polysaccharide are complexed with the indicator. The intensities of the color will be graduated to correspond to varying color intensities formed as a result of the varying concentration amounts of bioactive polysaccharides present in the aloe vera product. With the reader plate, the consumer simply pours the aloe vera sample or product into a container, preferably transparent, adds the complexing agent, and then swirls the container until the ingredients are thoroughly mixed. If a bioactive polysaccharide is present, a certain color will form as a result of the indicator complexing with the polysaccharide. The intensity of the color changes corresponds to the amount or concentration of polysaccharide present in the aloe vera product. The user then visually compares and matches the color formed with the corresponding color on the calibrated color reference chart, thereby informing the user that, firstly, a bioactive polysaccharide is present and, secondly, the approximate amount of bioactive polysaccharides present in the aloe vera product.

Further, a confirmatory test can be separately performed in another container using a second complexing or indicator agent in a manner similar to the method described above. The confirmatory test, if positive, further confirms the presence and the approximate amount of bioactive polysaccharide found in a sample of aloe-vera containing product.

Figure 2:
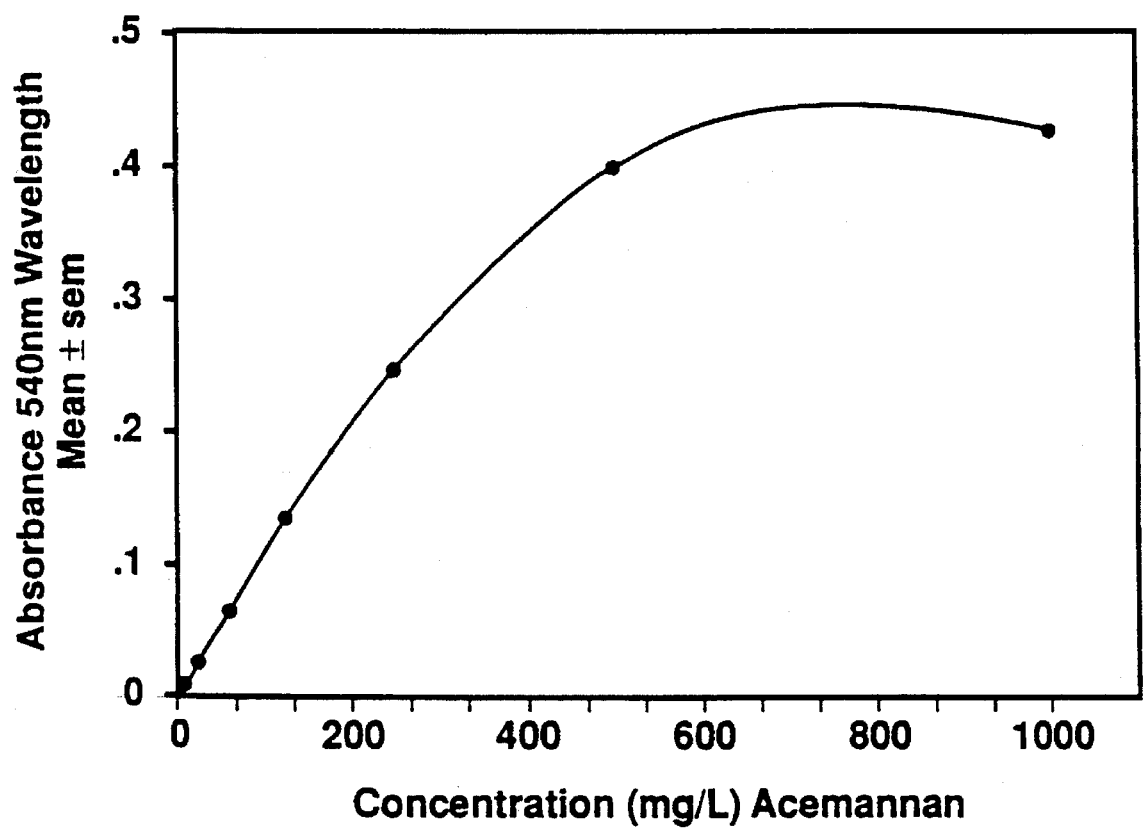
FIG. 2 is a graph showing a calibration plot of acemannan.
Figure 3:
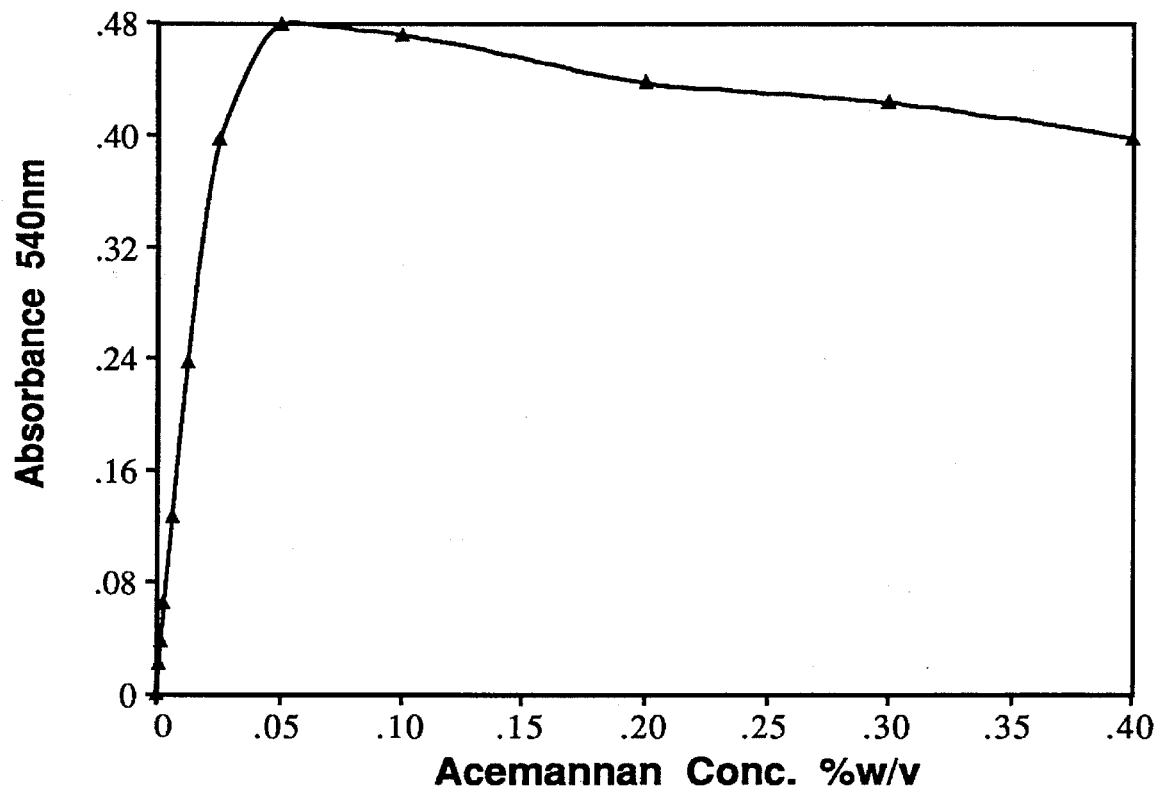
FIG. 3 is a graph showing the effect of acemannan concentration in μg/mL on the mean absorbance of the 540 nm acemannan-Congo Red complex.
Figure 4:
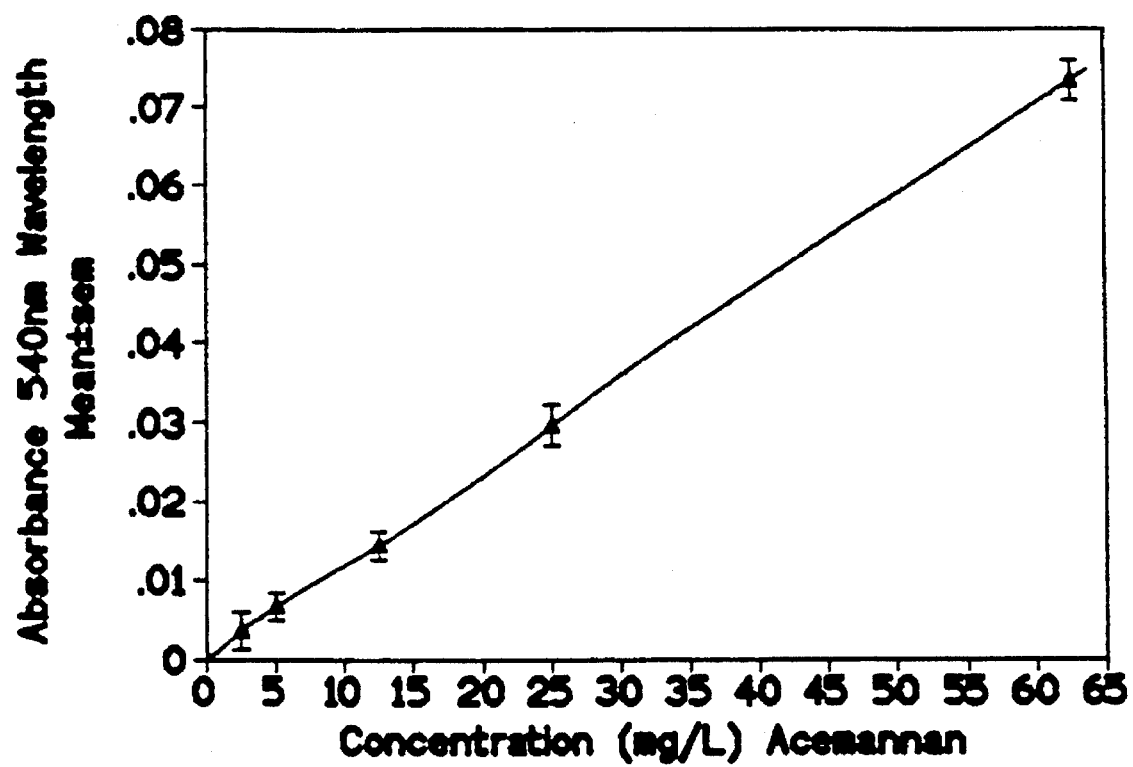
FIG. 4 is a graph showing the effect of acemannan concentration from 0 to 65 mg/L on the mean absorbance of the 540 nm acemannan-Congo Red complex.

As previously mentioned, the readings of the concentration are the most accurate when the aloe vera is present in the range of up to about 600 mg/L and more preferably up to about 300 mg/L or when the aloe vera is present in a concentration of from about 0.0008% w/v to about 0.2% w/v. These ranges are illustrated by FIGS. 2 and 3.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Analysis of Pure Acemannan by Congo Red Colorimetry

Materials: Acemannan, a linear polymer consisting of (1,4)-linked β-D-mannose residues with approximately one acetyl group per mannose residue, was extracted from the Aloe barbadensis Miller plant. The polysaccharide used for testing was free from protein and lipids. A 0.2M NaOH was prepared by diluting 50% weight per weight (w/w) NaOH with appropriate volume of deionized (DI) water. Congo Red indicator was dissolved in DI water to a concentration of $2\times10^{-4}M$. The instrument used was a Perkin Elmer, UV-VIS Coleman 55 spectrophotometer.

Method: Acemannan (2 mg) was weighed in an analytical balance and dissolved in 2 mL DI water to give a 1 mg/mL concentration. Several dilution of the solution (ranging from 2x to 400x) were made, giving a working solution including the stock solution, ranging from $2.5\times10^{-4}$–0.1% w/v or (2.5–1000 ppm) in acemannan. Aliquot samples (400 μL) of each concentration level was transferred into borosilicate glass vials. To each vial was added 500 μL of 0.2M NaOH with slight vortexing to mix. Then 100 μL of $2\times10^{-4}M$ aqueous Congo Red solution was added and mixed. The mixture was left at room temperature for 20 minutes before absorbance reading was taken at 540 nm wavelength of the Perkin Elmer spectrophotometer. The results are tabulated in the following Table:

TABLE 1

Absorbance Versus Concentration of Acemannan

| Absorbance Mean + SEM (n = 3) | Acemannan (ppm) | Concentration % w/v |
|---|---|---|
| 0.000 | 0 | 0 |
| 0.004 ± .002 | 2.5 | $2.5 \times 10^{-4}$ |
| 0.007 ± .001 | 5.0 | $5.0 \times 10^{-4}$ |
| 0.014 ± .002 | 12.5 | $1.25 \times 10^{-3}$ |
| 0.030 ± .003 | 25.0 | $2.5 \times 10^{-3}$ |
| 0.073 ± .003 | 62.5 | $6.25 \times 10^{-3}$ |
| 0.151 ± .002 | 125 | $1.25 \times 10^{-2}$ |
| 0.271 ± .003 | 250 | $2.5 \times 10^{-2}$ |
| 0.438 ± .002 | 500 | $5 \times 10^{-2}$ |
| 0.469 ± .004 | 1000 | $1 \times 10^{-1}$ |

Results and Discussion

FIG. 1 shows an overlaid spectra of Congo Red and Congo Red acemannan scans in the visible region of the spectrophotometer. The wavelength maximum shifted from 488 to 540 nm. A plot of the mean absorbance (n=3) against acemannan concentration in mg/L produced a curve demonstrating linearity from 0 to about 300 mg/L acemannan (FIG. 2). This portion of the curve can be used to quantify acemannan and other polysaccharides demonstrating similar characteristics. Between about 300 mg/L and about 700 mg/L, the curve showed an upward trend before slowly heading downward. Higher concentrations of acemannan' resulted in slight lowering of absorbance. This plot profile mimics cell receptor-mediated interaction observed in cell antigen interactions leading to immunological responses. This observation demonstrates that Congo Red polysaccharide complex formation can be used as a model for in vitro qualitative and quantitative evaluation of immunomodulating bioactive polysaccharide, such as acemannan.

EXAMPLE II

Analysis of Varying Concentration of Pure Acemannan

Acemannan (10 mg) was dissolved in 2.5 mL DI water to a homogeneous viscous liquid of 0.4% w/v acemannan. Aliquots of the liquid were transferred to vials and diluted to varying acemannan concentrations ranging from 0.0008 to 0.4% w/v. An aliquot (400 μL) of each concentration level was transferred to a sample tube labeled appropriately with the acemannan concentration content. Then 500 μL of 0.2M base was added and vortexed, followed by addition of 100 μL of $2\times10^{-4}$M Congo Red solution. The final base and Congo Red concentrations were 0 1M and $2\times10^{-5}$M respectively Absorbance of the samples was measured after 20 min. at 540nm wavelength using a reference blank containing 0% acemannan.

Results and Discussion

A plot of absorbance against acemannan concentration (FIG. 3) demonstrated a sharp increase in absorbance from 0.022 at 0.0008% w/v to 0.479 at 0.05% w/v then the absorbance decreased gradually to about 0.400 at 0.4% w/v acemannan. The acemannan Congo Red complex exhibited optimal maximum absorbance dependent on acemannan concentration. This is similar to the optimal doses observed for antitumor polysaccharides. As such, the Congo Red wavelength absorption shift can be used as an in vitro diagnostic test for development of antitumor agents such as acemannan.

EXAMPLE III

Quantitation of Aloe Vera Solid in Different Aloe Vera Beverages

Materials: Aloe vera solid (prepared from an in-house grown aloe vera plant) was reconstituted to different concentrations in aqueous medium. Aloe vera-containing beverages were obtained from different aloe vera processors. Non-aloe polysaccharides were purchased from Commercial Chemical Companies. These included Dextran MW 150,000, Lot #83F-02241 (Sigma Chemical Co., St. Louis, Mo.); Locust bean gum, Lot #B.8506 (TIC Gums, Inc., Belcamp, Md.); Guar gum, Lot #HF07303LZ (Aldrich Chemical Co., Inc., Milwaukee, Wis.); Dextrin Cat. #101517 (ICN Nutritional Biochemical Co., Cleveland, Ohio). Other materials used included Dextrose, Lot #733,569 (Fisher Scientific Co.) and Congo Red Lot #116F-3682 (Sigma Chemical Co., St. Louis, Mo.).

Preparation of Aloe Vera Reference Standard

Two leaves weighing approximately one pound (1 lb.) were cut off from a plant grown in-house. The outer leaf rind was removed and the clear gel from the inner portion of the leaf was homogenized. The homogenate was filtered through four layers of cheese cloth to remove fibrous materials, including pectic solids. The viscous filtrate was transferred into freeze drier sample glass holders and then frozen in liquid nitrogen. The frozen gel was freeze-dried in a bench top drier (Virtis Model #10-135). The dried solid was finely ground, weighed (800 mg) and stored in a desiccator for four days. After four days, the sample was reweighed with no appreciable weight change observed.

Preparation of Aloe Vera Reference Calibration Standard Curve

Approximately 20 mg of the reference standard, made up of freeze-dried aloe vera gel, was accurately weighed and transferred into a vial. The freeze-dried aloe vera gel was obtained by first removing rind from aloe vera leaves, subsequently homogenizing the resultant gel, then filtering to remove cellulosic fibrous material, followed by freeze drying. The solid was dissolved in 2 mL of DI water to give a concentration of 1.0% w/v. This concentration was arbitrarily assigned "200% aloe vera value." The solution was passed through a 1.2 μm membrane filter as part of the standard assay procedure. Subsequent aqueous dilutions of aliquots from the filtered solution were prepared to obtain various concentration levels in 400 μL solution. The color was developed by adding 500 μL of 0.2M NaOH to each sample vial, followed by adding 100 μL of $2\times10^{-4}$M Congo Red. The vial was vortexed to mix and the color developed immediately; however, the reaction mixture was left at room temperature for more than 20 minutes before absorbance was read at 540 nm wavelength in a Perkin-Elmer, UV-VIS Coleman 55 spectrophotometer. Each concentration level was repeated three times and the mean with standard error of mean was estimated as follows:

TABLE 2

Absorbance Versus Concentration of Aloe Vera Gel

| Absorbance (Means ± SEM) | Percent of Standard Freeze-Dried Aloe Vera Gel Solid (% w/v) | Percent Aloe Vera Value (%) |
|---|---|---|
| 0.000 ± 0 | 0.00 | 0.00 |
| 0.012 ± .002 | 0.0039 | 0.784 |
| 0.028 ± .001 | 0.0078 | 1.56 |
| 0.049 ± .001 | 0.0156 | 3.12 |
| 0.084 ± .002 | 0.0312 | 6.25 |
| 0.134 ± .003 | 0.625 | 12.5 |
| 0.175 ± .005 | 0.125 | 25 |
| 0.245 ± .004 | 0.25 | 50 |
| 0.386 ± .001 | 0.5 | 100 |
| 0.544 ± .005 | 1.0 | 200 |

Analysis of Commercial Aloe Vera Beverages and Drinks Sample Preparation

Each bottle containing the aloe vera beverage was shaken vigorously before an aliquot sample was taken for analysis. The aliquot was filtered through 1.2 μm membrane filter (Acrodisc®, Gelman). Filtered sample aliquot was analyzed by transferring 400 μL of the product into a vial, then adding successively 500 μL of 0.2M NaOH and 100 μL of Congo Red ($4 \times 10^{-4}$M) for a total of 1000 μL solution. The reaction mixture was allowed to stand at room temperature for 20 minutes before absorption reading was taken at 540 nm wavelength. Each product was analyzed in triplicate and the mean was used to determine the percent aloe vera gel bioactive polysaccharide in the beverage.

TABLE 3

Percent Aloe Vera Value In Commercial Beverages

| Sample ID | Mean Abs (n = 3) | % Aloe Vera Value |
|---|---|---|
| Herbal Life 20611 | 0.105 | 9 |
| An. Dream | 0.135 | 13 |
| Aloe vera leaf in bottle Aus 041393 | 0.188 | 30 |
| 11 year old juice | 0.205 | 36 |
| Life Stream | 0.215 | 39 |
| de Veras | 0.216 | 40 |
| New Image | 0.244 | 50 |
| Caraloe 308251 | 0.246 | 50 |
| Caraloe 307031 | 0.247 | 51 |
| Aloe Fresh | 0.281 | 63 |
| PJ 16 | 0.284 | 64 |
| PH 41 8/10/93 | 0.316 | 75 |
| MK 76 10/7/91 | 0.349 | 87 |
| PH 37 8/13/93 | 0.372 | 95 |
| PH 60 9/1/93 | 0.399 | 108 |
| PJ 27 | 0.414 | 118 |
| PH 47 8/19/93 | 0.416 | 131 |

Results and Discussion

The technique is based on the molecular interaction between aloe polysaccharide and Congo Red—a coloring agent under low base concentration (1M). Congo Red absorption maximum shifted to 540 nm wavelength making it possible to quantify the bioactive polysaccharide present in the aloe-vera containing product. Data in Table 2 were used to generate a calibration curve of absorbance against concentration of aloe vera to arrive at the aloe vera values in Table 3. The aloe vera bioactive polysaccharide concentration of an aloe beverage can be directly estimated from the standard calibration plot. Table 3 shows contents of aloe vera gel bioactive polysaccharide expressed as % aloe vera value of some commercially available aloe beverages. Content of aloe vera gel bioactive polysaccharide of the beverages ranged from 10% to 130% based on our defined criteria of one percent (w/v) aloe solid equivalent to 200% aloe vera value.

EXAMPLE IV

Colorimetric Assays of Various Polysaccharides Using Congo Red

Sample Preparation and Analysis

Aloe vera gel solid (from in-house grown plant) and each compound (non-aloe polysaccharides) were weighed separately and then dissolved in DI water to a concentration of 1% w/v solution. The solutions were filtered through 1.2 μm membrane (Acrodisc Gelman). The filtered solutions were serially diluted (1X-20X) to give analyte concentration (w/v) similar in each product.

Aliquots (400 μL) from each concentration level were transferred into borosilicate reaction vials with screw caps in triplicates. A 500 μL 0.2M NaOH base was added to each reaction vial, followed by a 100 μL of Congo Red colorizing agent ($2 \times 10^{-4}$M). The reaction mixtures were shaken vigorously and allowed to stand for about 20 minutes at room temperature. Absorbance measurement was taken for each vial in a single beam UV-VIS spectrophotometer (Perkin-Elmer).

TABLE 4

Absorbance of Aloe Vera Gel Polysaccharide Compared to Non-Aloe Polysaccharides

| % Sample (w/v) | Aloe gel (Abs) | Dextrin (Abs) | Guar Gum (Abs) | Locust Gum (Abs) | Dextran (Abs) |
|---|---|---|---|---|---|
| 0.05 | 0.106 | 0.004 | 0.002 | 0.001 | 0.004 |
| 0.062 | 0.124 | 0.005 | 0.004 | 0.002 | 0.002 |
| 0.125 | 0.169 | 0.010 | 0.005 | 0.005 | 0.007 |
| 0.25 | 0.239 | 0.020 | 0.005 | 0.003 | 0.006 |
| 0.50 | 0.384 | 0.040 | 0.008 | 0.001 | 0.004 |
| 1.0 | 0.533 | 0.079 | 0.007 | 0.010 | 0.008 |

Figure 5:
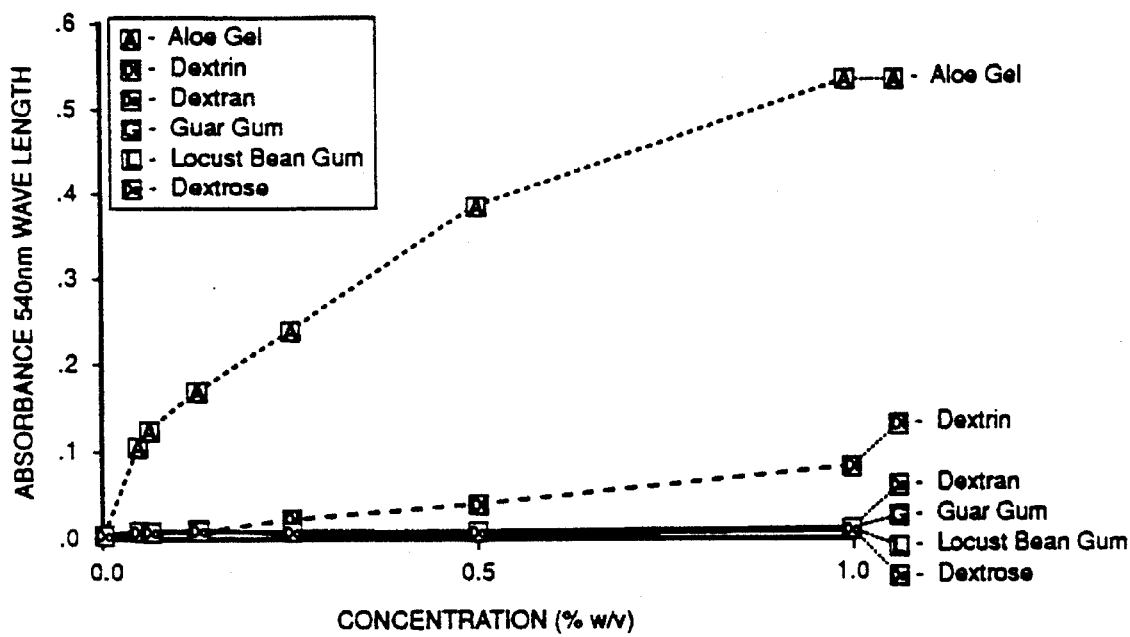
FIG. 5 is a graph showing the differences in the absorbance between aloe gel and other non-aloe polysaccharides.
Figure 6:
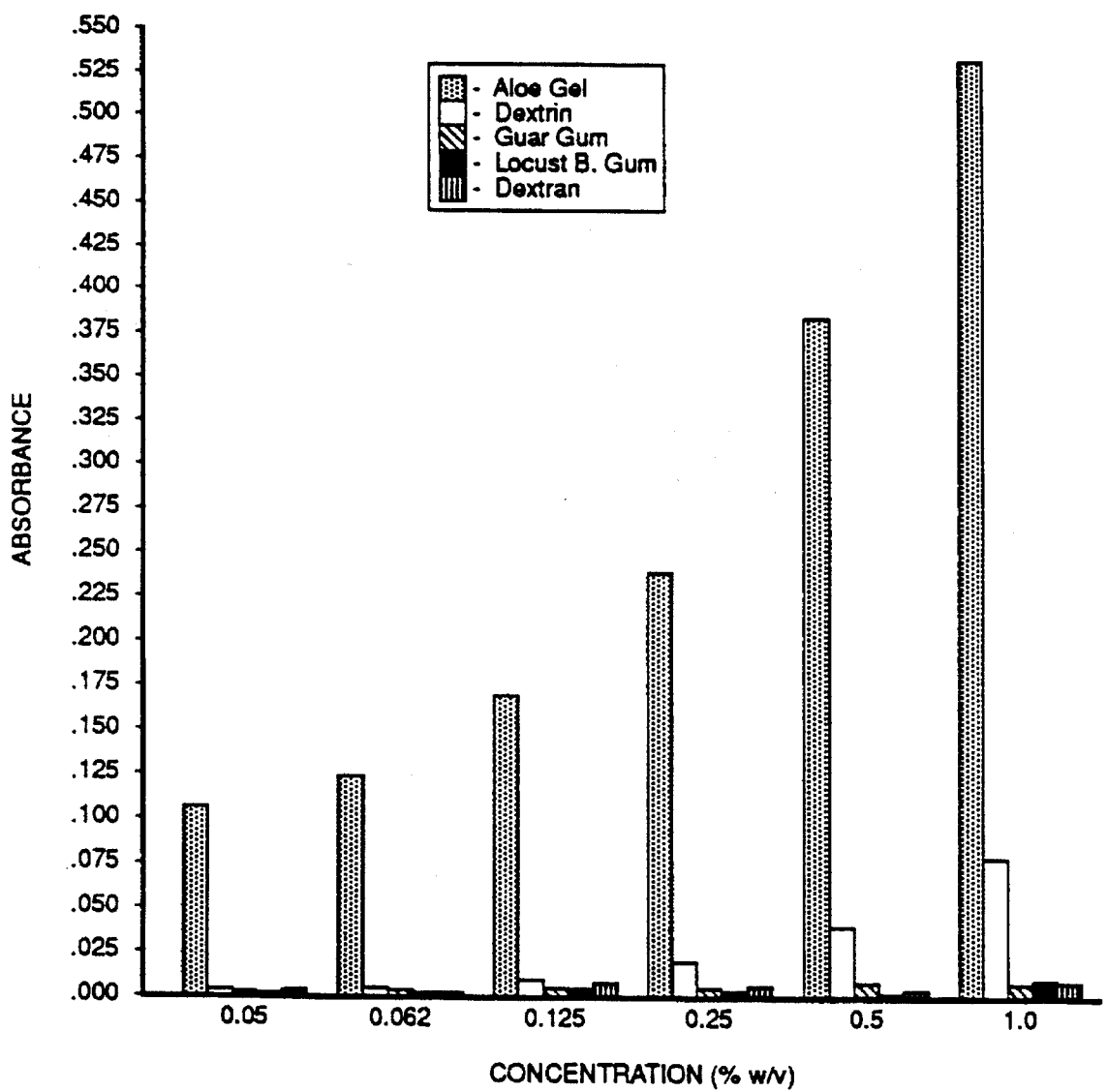
FIG. 6 is a bar graph demonstrating differences in color development by aloe vera polysaccharides compared to other polysaccharides commonly used to adulterate aloe juice.

The colorimetric assay was sensitive to specific polysaccharides found in aloe vera while remaining virtually non-responsive to other non-aloe polysaccharides (Table 4, FIGS. 5 and 6).

FIG. 6 is a bar diagram of the measured absorbance of different dilutions of aloe vera gel polysaccharide compared to other polysaccharides which are commonly used to adulterate aloe products. Data show that aloe vera gel polysaccharide can be detected and quantified after a more than 250-fold dilution (Table 2) in more than 200-fold dextran, guar gum, locust bean gum, (Table 4) proteins, dextrose, oligosaccharides and other monosaccharides. This is a significant invention because the authentic aloe vera gel polysaccharide in a product can be easily determined even at a very low concentration and in the presence of large amounts of non-aloe vera polysaccharides and mono-saccharides, which may be used to adulterate an aloe vera-containing product.

EXAMPLE V

Influence of pH on the Absorbance of Acemannan-Congo Red Complex

Method

Acemannan (10mg) was dissolved in 5mL 0.05% w/v aqueous sodium azide to give a 2 mg/mL concentration. Aliquot samples (100μL) of the solution was transferred into borosilicate glass vials (eleven) labelled from pH 2 to 12. Corresponding blanks consisting of 100 μL of 0.05% w/v sodium azide were also prepared. Eight hundred (800 μL) microliters of appropriate buffer and 100 μL of Congo Red solution $2 \times 10^{-4}$ M were added to both samples and blanks. The mixture was left at room temperature for 20 minutes before absorbance was read at 540nm wavelength of Perkin-Elmer spectrophotometer.

Buffer solutions were prepared by mixing appropriate volumes of solution A (0.2M boric acid and 0.05M citric acid) and solution B (0.1M trisodium phosphate). Shugar GJ, Dean JA. *The Chemist's Ready Reference Handbook*, McGraw-Hill Publishing Co., New York, 1989.

Results

Figure 7:
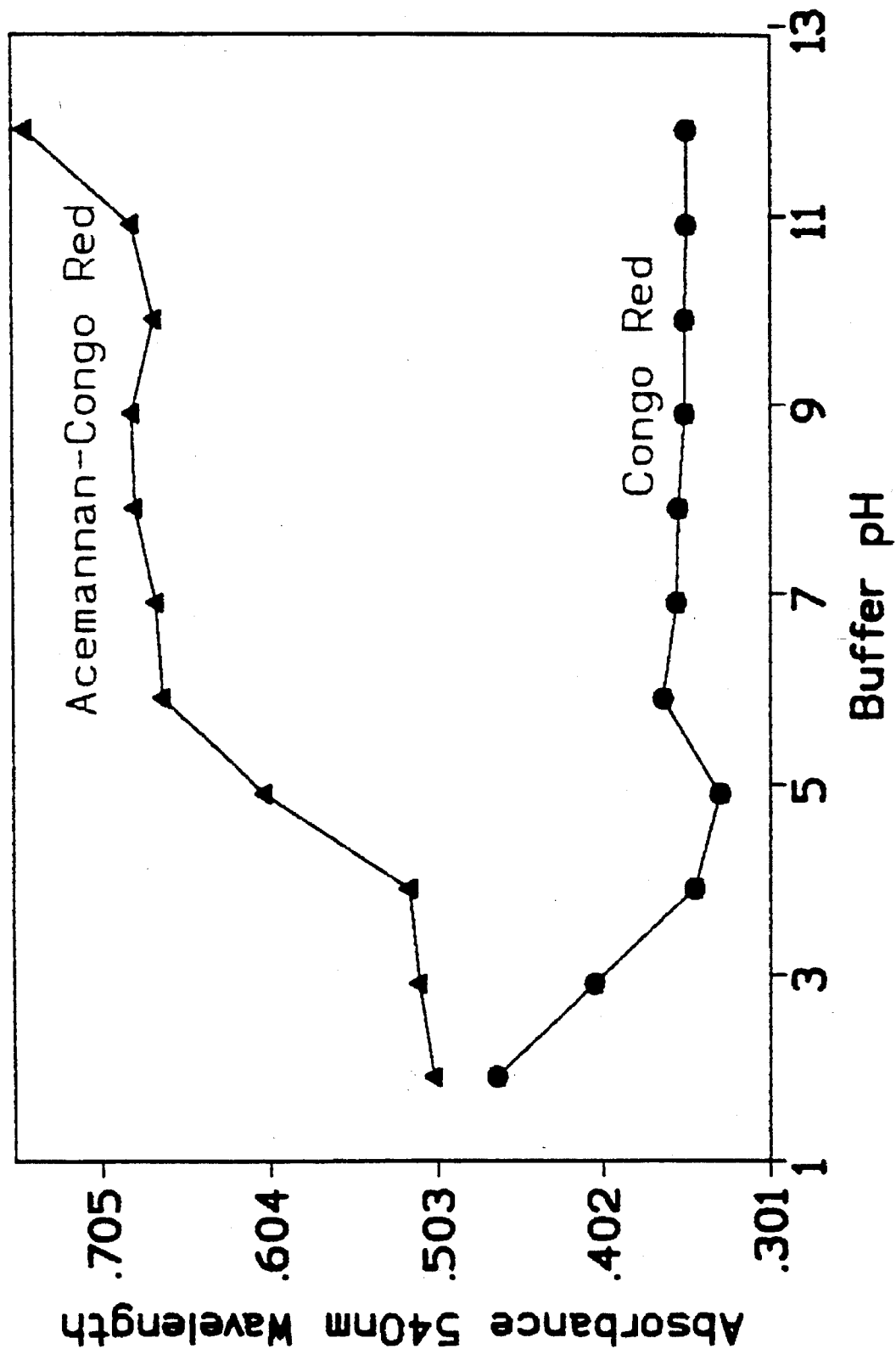
FIG. 7 shows the differences in absorbance of acemannan-Congo Red and Congo Red under different pH conditions.

FIG. 7 demonstrates that the difference in absorbance between acemannan-Congo Red complex and the Congo Red alone is somewhat pH dependent. There is a large difference in absorbance for pH's ranging from about 4 to about 14. The maximum difference appears to be between about pH 12 and about pH 14.

EXAMPLE VI

Color-Complex Formation Between Various Polysaccharides and Various Dyes

Method

Each polysaccharide was weighed in an analytical balance and dissolved in DI water to give a 2 mg/mL concentration. Aliquot sample (400 μL) of the polysaccharide sample was transferred into borosilicate glass vials. To each vial was added 500 μL of 0.2M NaOH with slight vortexing to mix. Then 100 μL of $2 \times 10^{-4}$ aqueous dye solution was added and mixed. The mixture was left at room temperature for 20 minutes before absorbance reading was taken at 540 nm wavelength on a Perkin-Elmer spectrophotometer. Each polysaccharide was tested with all the dyes and a reaction blank of the dye without the polysaccharide was used to determine if the polysaccharide formed color-complex.

Results

Color formation with various polysaccharides in the presence of dyes was investigated, The result was tabulated and the degree of color development was graded as shown in Table 5.

TABLE 5

Coloration of Polysaccharides with Different Dyes
Coloration of Polysaccharides with Dyes

| DYES | POLYSACCHARIDES | | | | | | | |
|---|---|---|---|---|---|---|---|---|
|  | Dextran 531K | Acemannan | Gharo Gum | Arabic Gum | Dextran | Methyl Cellulose | Xanthan Gum | Tragacanth Gum |
| Congo Red | — | +++ | —+ | —+ | —+ | ++ | —+ | —+ |
| Anline Blue | — | —+ | — | — | — | — | — | — |
| Brilliant Blue | — | —+ | — | — | — | — | — | — |
| Alclan Blue | — | — | — | — | — | — | — | — |
| Acridine Orange | — | —+ | — | — | — | — | — | — |
| Methyl Orange | — | — | — | — | — | — | — | — |
| Crystal Violet | — | + | — | — | — | — | — | — |
| Toluldine Blue | — | + | — | — | — | — | — | — |

| DYES | Starch | CMC | Malto Dextran | Carragenan I | Carragenan II | Guaica Gum | Karaya Gum |
|---|---|---|---|---|---|---|---|
| Congo Red | — | —+ | — | —+ | —+ | — | —+ |
| Anline Blue | — | — | — | — | — | — | — |
| Brilliant Blue | — | — | — | — | — | — | — |
| Aician Blue | — | — | — | — | — | — | — |
| Acridine Orange | — | — | — | — | — | — | — |
| Methyl Orange | — | — | — | — | — | — | — |
| Crystal Violet | — | — | — | — | — | — | — |
| Toluldine Blue | — | — | — | — | — | — | — |

Color development is graded as follows:
— = Not Different from blank
—+ = Slightly Different from blank
+ = Different from blank
++ = Significantly Different from blank
+++ = Very Significantly Different from blank Acemannan was intensely colored by Congo Red dye. Congo Red stained methylcellulose significantly. The dye also developed slight color with arabic gum, xanthan gum, tragacanth, CMC, etc. There was no color developed for dextran, starch, maltodextrin, guaica gum. Acemannan was slightly colored by aniline blue, brilliant blue, crystal violet and toluidine blue. Generally, the test that has practical utility is the one in which the color developed is either significantly different from the blank (as indicated by ++) or very significantly different from the blank (as indicated by +++).

As can be seen from Table 5, each of Crystal Violet and Toluidine Blue forms a color complex with acemannan but not with other polysaccharides tested. Accordingly, each of the dyes Crystal Violet and Toluidine Blue can be used as a separate confirmatory indicator agent to confirm the presence of acemannan when the formation of a Congo Red-acemannan complex has been determined independently.

EXAMPLE VII

Analysis of Acemannan Protein Binding

Method

A solution of thyroglobulin Lot #C622 (Pharmacia) was prepared by dissolving 5.2 mg of the protein in 5 mL of DI water. Acemannan (10 mg) Lot #010302 (Carrington Labs) was dissolved in 10 mL DI water to a concentration of 1 mg/mL solution. Acemannan 200 µL (200 µg) was pipetted into seven separate vials (#s2-8). Two other vials #1 and #9 contained 0 µg acemannan. A varying amount of the protein (10–208 µg) was added to vials #3-9, respectively, while vials #1 and #2 contained 0 µg thyroglobulin. All the vials (#s1-9) were reconstituted to 400 µL volume with DI water. Then 500 µL of 0.2M NaOH was added to each vial followed by 100 µL of $2 \times 10^{-4}$ M Congo Red. The vials were shaken vigorously to mix and then left at room temperature for about 20 minutes. Absorbance measurement was taken in a Perkin-Elmer UV-VIS spectrophotometer at 540 nm wavelength. Four replicate measurements were taken for each data point.

The experiment was repeated exactly as above, except that varying amounts of acemannan were used while thyroglobulin was kept constant (Tables 6 & 7).

TABLE 6

Absorbance of Acemannan and Congo Red in Varying Amounts of Thyroglobulin

| Acemannan† (µL) | Thyroglob†† (µL) | Water (µL) | Base* (µL) | Congo Red** (µL) | Absorbance Mean + 95% |
|---|---|---|---|---|---|
| 0 | 0 | 400 | 500 | 100 | 0.00 |
| 200 | 0 | 200 | 500 | 100 | 0.456 ± .019 |
| 200 | 10 | 190 | 500 | 100 | 0.443 ± .010 |
| 200 | 25 | 175 | 500 | 100 | 0.408 ± .010 |
| 200 | 50 | 150 | 500 | 100 | 0.355 ± .004 |
| 200 | 100 | 100 | 500 | 100 | 0.255 ± .005 |
| 200 | 150 | 50 | 500 | 100 | 0.175 ± .006 |
| 200 | 200 | 0 | 500 | 100 | 0.123 ± .004 |
| 0 | 200 | 200 | 500 | 100 | 0.015 ± .00 |

†Acemannan conc. 1 µg/µL
††Thyroglobulin conc. 1.04 µg/µL
*Base conc. 0.2M NaOH
**Congo Red conc. $2 \times 10^{-4}$ M

TABLE 7

Absorbance of Thyroglobulin and Congo Red in Varying Amounts of Acemannan

| Acemannan† (µL) | Thyroglob†† (µL) | Water (µL) | Base* (µL) | Red** (µL) | Absorbance Mean + 95% |
|---|---|---|---|---|---|
| 0 | 0 | 400 | 500 | 100 | 0.00 |
| 0 | 200 | 200 | 500 | 100 | 0.008 ± .004 |
| 10 | 200 | 190 | 500 | 100 | 0.021 ± .006 |
| 25 | 200 | 175 | 500 | 100 | 0.028 ± .002 |
| 50 | 200 | 150 | 500 | 100 | 0.049 ± .004 |
| 100 | 200 | 100 | 500 | 100 | 0.078 ± .003 |
| 150 | 200 | 50 | 500 | 100 | 0.100 ± .003 |
| 200 | 200 | 0 | 500 | 100 | 0.112 ± .013 |
| 200 | 0 | 200 | 500 | 100 | 0.461 ± .007 |

Figure 8:
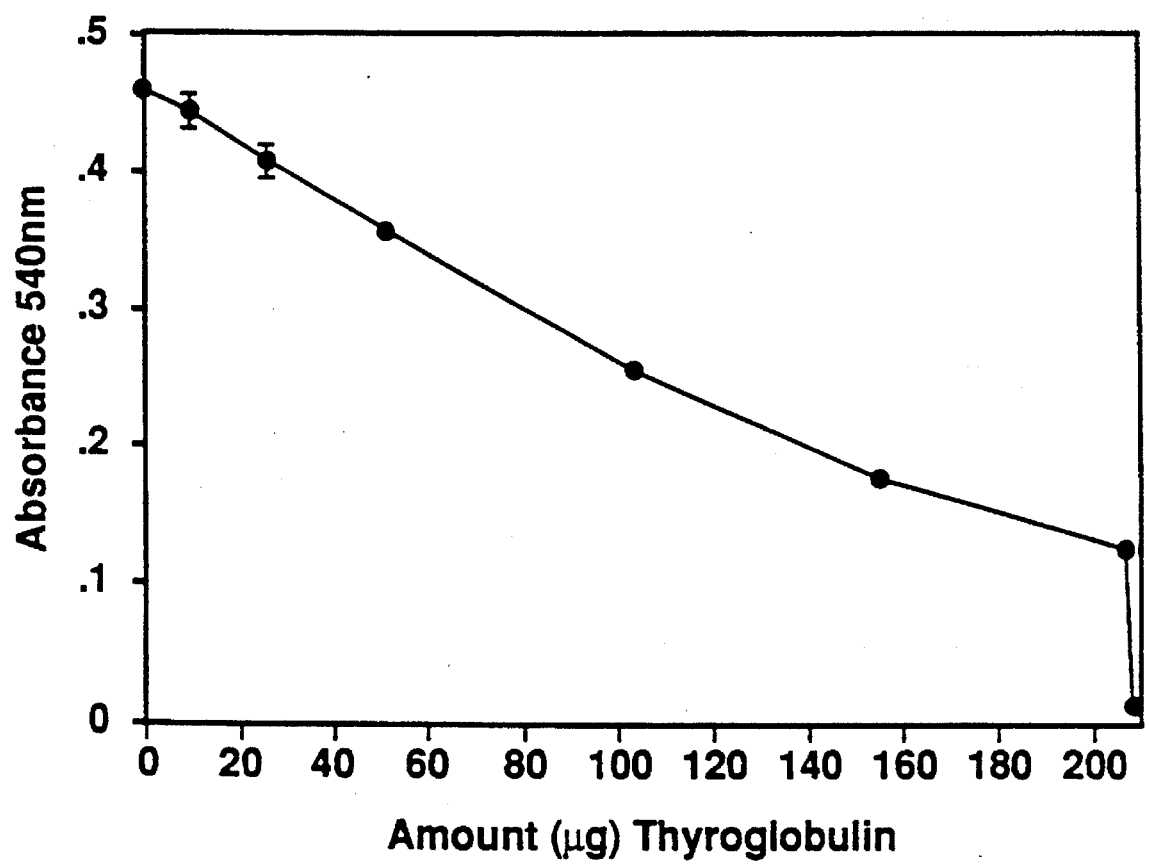
FIG. 8 is a graph showing the effect of thyroglobulin concentration in μg on the mean absorbance of the 540 nm acemannan-Congo Red complex.

†Acemannan conc. 1 µg/µL
††Thyroglobulin conc. 1.04 µg/µL
*Base conc. 0.2M NaOH
**Congo Red conc. $2 \times 10^{-4}$ M Results & Discussion A plot of mean absorbance versus amount of protein (FIG. 8) demonstrates a significant reduction in absorbance with increased protein amount. Acemannan Congo Red color absorption was significantly reduced when the protein (208 µg) was added (0.123) compared to acemannan absorption without the protein (0.456). Thyroglobulin (208 µg) alone had no significant absorption (0.015).

Figure 9:
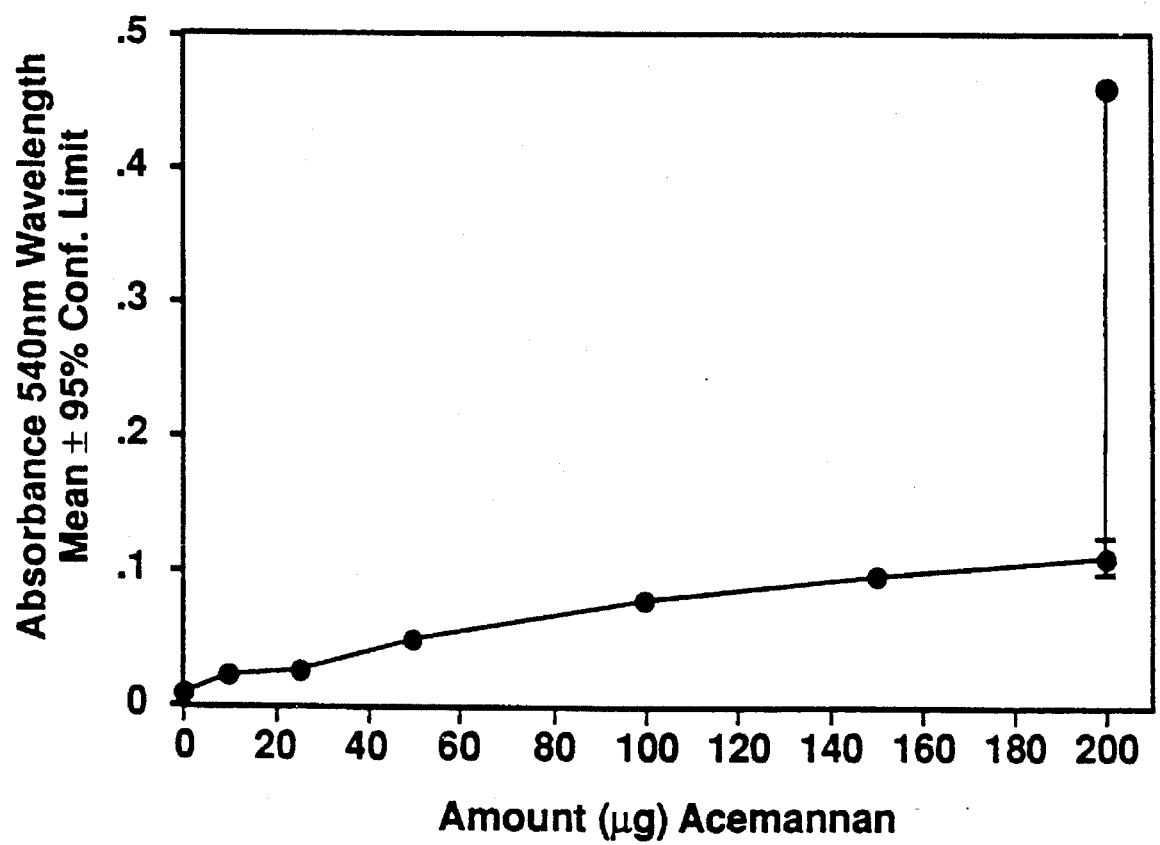
FIG. 9 is a graph showing the effect of a constant amount of thyroglobulin in varying amounts of acemannan on the mean absorbance of the 540 nm acemannan-Congo Red complex.

When the amount of acemannan was varied (0–200 µg) while the protein amount was kept constant (208 µg), the absorbance of the acemannan Congo Red complex was equally reduced as illustrated in FIG. 9. The absorbance of 0.112 with the protein compared to 0.461 without the protein demonstrated a significant reduction in the presence of the protein. The protein by itself did not absorb significantly (0.008) at the 540 nm wavelength.

The data shows that acemannan binds to proteins much stronger than it binds to the Congo Red. Since Congo Red alone does not absorb strongly at 540 nm wavelength, the technique affords a very powerful assay for monitoring and evaluating acemannan as well as serum proteins and other bioactive polysaccharides that bind to Congo Red.

The foregoing detailed description is to be clearly understood as being given by way of illustration and example only, the spirit and scope of the present invention being limited solely by the appended claims.

What is claimed is:

1. A method of determining and confirming the presence or amount of a bioactive polysaccharide in a product, said method comprising the steps of:

bringing into contact a first aliquot of said product with a first calorimetric complexing agent in a first suitable medium to form a first reaction mixture;

allowing a first color change to occur in said first reaction mixture;

detecting said first color change in said first reaction mixture;

comparing the first detected color change with first standard color changes generated by reacting said first calorimetric complexing agent with different known amounts of said bioactive polysaccharide, wherein differences between said first color changes compared are dependent upon the presence or amount of said bioactive polysaccharide in said product;

separately bringing into contact a second aliquot of said product with a second calorimetric complexing agent in a second suitable medium to form a second reaction mixture;

allowing a second color change to occur in said second reaction mixture;

detecting said second color change in said second reaction mixture; and comparing the detected second color change with second standard color changes generated by reacting said second calorimetric complexing agent with different known amounts of said bioactive polysaccharide, wherein differences between said second color changes compared are dependent upon the presence or amount of said bioactive polysaccharide in said sample and wherein said second color change confirms the determination of the presence or amount of said bioactive polysaccharide in said product by said first calorimetric complexing agent.

2. A method of determining the presence or amount of a bioactive aloe vera polysaccharide in a product, said method comprising the steps of:

bringing into contact an aliquot of said product with a colorimetric complexing agent in a suitable medium to form a reaction mixture;

allowing color change to occur in said reaction mixture;

detecting said color change in said reaction mixture; and comparing the detected color change with standard color changes generated by reacting said colorimetric complexing agent with different known amounts of said bioactive aloe vera polysaccharide, wherein differences between the color changes compared are dependent upon the presence or amount of said bioactive aloe vera polysaccharide in said product.

3. The method of claim 2, wherein said product comprises a beverage.

4. The method of claim 2, wherein said bioactive aloe vera polysaccharide comprises polymeric mannan derivative.

5. The method of claim 2, wherein said bioactive aloe vera polysaccharide comprises acemannan.

6. The method of claim 2, wherein said colorimetric complexing agent is Congo Red.

7. The method of claim 2, wherein said colorimetric complexing agent is selected from the group consisting of Crystal Violet and Toluidine Blue.

8. The method of claim 1, wherein said suitable medium comprises a basic solution or an aqueous buffer solution.

9. The method of claim 8, wherein said aqueous buffer solution has a pH in the range of from about 4 to about 14.

10. The method of claim 8, wherein said aqueous buffer solution has a pH in the range of from about 6 to about 14.

11. The method of claim 8, wherein said aqueous buffer solution has a pH in the range of from about 12 to about 14.

12. The method of claim 2, wherein said amount of said bioactive aloe vera polysaccharide is below about 600 mg per kilogram of said product.

13. The method of claim 2, wherein said amount of said bioactive aloe vera polysaccharide is below about 300 mg per kilogram of said product.

14. The method of claim 2 further comprising the steps of:

separately bringing into contact a second aliquot of said product with a second colorimetric complexing agent in a second suitable medium to form a second reaction mixture;

allowing second color change to occur in said second reaction mixture;

detecting said second color change in said second reaction mixture; and comparing the detected second color change with second standard color changes generated by reacting said second colorimetric complexing agent with different known amounts of said bioactive aloe vera polysaccharide, wherein differences between the second color changes compared are dependent upon the presence or amount of said bioactive aloe vera polysaccharide in said product and wherein said second color change confirms the determination of the presence or amount of said bioactive aloe vera polysaccharide in said product by said colorimetric complexing agent.

15. A method of determining the presence or amount of acemannan in an aloe vera-containing product, said method comprising the steps of:

bringing into contact an aliquot of said product with Congo Red in a suitable medium to form a reaction mixture;

allowing color change to occur in said reaction mixture;

detecting said color change in said reaction mixture; and comparing the detected color change with standard color changes generated by reacting said Congo Red with different known amounts of said acemannan, wherein differences between the color changes compared are dependent upon the presence or amount of said acemannan in said product.

16. The method of claim 15, wherein said product comprises a beverage.

17. The method of claim 15, wherein said medium is an aqueous solution having a pH in the range of from about 4 to about 14.

18. The method of claim 15, wherein said medium is an aqueous solution having a pH in the range of from about 6 to about 14.

19. The method of claim 15, wherein said medium is an aqueous solution having a pH in the range of from about 12 to about 14.

20. The method of claim 15, wherein said amount of said acemannan is below about 600 mg per kilogram of said product.

21. The method of claim 15, wherein said amount of said acemannan is below about 300 mg per kilogram of said product.

22. A method of determining and confirming the presence or amount of acemannan in an aloe vera-containing product, said method comprising the steps of:

bringing into contact a first aliquot of said product with a first colorimetric complexing agent in a first suitable medium to form a first reaction mixture;

allowing a first color change to occur in said first reaction mixture;

detecting said first color change in said first reaction mixture;

comparing the first detected color change with first standard color changes generated by reacting said first colorimetric complexing agent with different known amounts of said acemannan, wherein differences between said first color changes compared are dependent upon the presence or amount of said acemannan in said product;

separately bringing into contact a second aliquot of said sample with a second colorimetric complexing agent in a second suitable medium to form a second reaction mixture;

allowing a second color change to occur in said second reaction mixture;

detecting said second color change in said second reaction mixture; and comparing the detected second color change with second standard color changes generated by reacting said second colorimetric complexing agent with different known amounts of said acemannan, wherein differences between said second color changes compared are dependent upon the presence or amount of said acemannan in said product and wherein said second color change confirms the determination of the presence or amount of said acemannan in said product by said first colorimetric complexing agent.

23. The method of claim 22, wherein said product comprises a beverage.

24. The method of claim 22, wherein said first and second media are aqueous solutions having a pH in the range of from about 4 to about 14.

25. The method of claim 22, wherein said first and second media are aqueous solutions having a pH in the range of from about 6 to about 14.

26. The method of claim 22, wherein said first and second media are aqueous solutions having a pH in the range of from about 12 to about 14.

27. The method of claim 22, wherein said amount of said acemannan is below about 600 mg per kilogram of said product.

28. The method of claim 22, wherein said amount of said acemannan is below about 300 mg per kilogram of said product.

29. The method of claim 22, wherein said first colorimetric complexing agent is selected from the group consisting of Congo Red, Crystal Violet and Toluidine Blue.

30. The method of claim 22, wherein said second colorimetric complexing agent is selected from the group consisting of Congo Red, Crystal Violet and Toluidine Blue.

31. A method of determining and confirming the presence or amount of a bioactive aloe vera polysaccharide in a product, said method comprising the steps of:

bringing into contact a first aliquot of said product with a first colorimetric complexing agent in a first suitable medium to form a first reaction mixture;

allowing a first color change to occur in said first reaction mixture;

detecting said first color change in said first reaction mixture;

comparing the first detected color change with first standard color changes generated by reacting said first colorimetric complexing agent with different known amounts of said bioactive aloe vera polysaccharide, wherein differences between said first color changes compared are dependent upon the presence or amount of said bioactive aloe vera polysaccharide in said product;

separately bringing into contact a second aliquot of said sample with a second colorimetric complexing agent in a second suitable medium to form a second reaction mixture;

allowing a second color change to occur in said second reaction mixture;

detecting said second color change in said second reaction mixture; and comparing the detected second color change with second standard color changes generated by reacting said second colorimetric complexing agent with different known amounts of said bioactive aloe vera polysaccharide, wherein differences between said second color changes compared are dependent upon the presence or amount of said bioactive aloe vera polysaccharide in said product and wherein said second color change confirms the determination of the presence or amount of said bioactive aloe vera polysaccharide in said product by said first colorimetric complexing agent.

32. The method of claim 31, wherein said product comprises a beverage.

33. The method of claim 31, wherein said first and second media are aqueous solutions having a pH in the range of from about 4 to about 14.

34. The method of claim 31, wherein said first and second media are aqueous solutions having a pH in the range of from about 6 to about 14.

35. The method of claim 31, wherein said first and second media are aqueous solutions having a pH in the range of from about 12 to about 14.

36. The method of claim 31, wherein said amount of said bioactive aloe vera polysaccharide is below about 600 mg per kilogram of said product.

37. The method of claim 31, wherein said amount of said bioactive aloe vera polysaccharide is below about 300 mg per kilogram of said product.

38. The method of claim 31, wherein said first colorimetric complexing agent is selected from the group consisting of Congo Red, Crystal Violet and Toluidine Blue.

39. The method of claim 31, wherein said second colorimetric complexing agent is selected from the group consisting of Congo Red, Crystal Violet and Toluidine Blue.

* * * * *

UNITED STATES PATENT AND TRADEMARK OFFICE
CERTIFICATE OF CORRECTION

PATENT NO. : 5,512,488
DATED : April 30, 1996
INVENTOR(S) : Eberendu et al.

It is certified that error appears in the above-indentified patent and that said Letters Patent is hereby corrected as shown below:

Col. 6, line 51, delete "consumer-can" and insert therefore -- consumer can --.

Col. 9, line 52, delete "0 1M" and insert therefore -- 0.1M --.

Col. 9, line 53, following "tively", insert -- . --.

Col. 11, line 20, following "Drinks", insert a paragraph break.

Col. 11, in Table 3, in line 2 under the heading "Sample ID", delete "An. Dream" and insert therefore -- Am. Dream --.

Col. 13, in Table 5, below the first occurrence of "Methyl Orange", insert a new line -- Evans Blue  -   -   -   -   -   -   -   -- .

UNITED STATES PATENT AND TRADEMARK OFFICE
CERTIFICATE OF CORRECTION

Page 2 of 3

PATENT NO. : 5,512,488
DATED : April 30, 1996
INVENTOR(S) : Eberendu et al.

It is certified that error appears in the above-indentified patent and that said Letters Patent is hereby corrected as shown below:

Col. 13, in Table 5, below the second occurrence of "Methyl Orange", insert a new line -- Evans Blue - - - - - - -- --.

Col. 13, in Table 5, delete both occurrences of the word "Toluldine" and insert therefore -- Toluidine --.

Col. 13, in Table 5, in the fourth line of the second chart, delete "Aician" and insert therefore -- Alclan --.

Col. 16, line 49, delete "calorimetric" and insert therefore -- colorimetric --.

Col. 16, line 57, delete "calorimetric" and insert therefore -- colorimetric --.

Col. 16, line 63, delete "calorimetric" and insert therefore -- colorimetric --.

Col. 17, line 5, delete "calorimetric" and insert therefore -- colorimetric --.

UNITED STATES PATENT AND TRADEMARK OFFICE
CERTIFICATE OF CORRECTION

PATENT NO. : 5,512,488
DATED : April 30, 1996
INVENTOR(S) : Eberendu et al.

It is certified that error appears in the above-indentified patent and that said Letters Patent is hereby corrected as shown below:

Col. 17, line 12, delete "calorimetric" and insert therefore -- colorimetric --.

Col. 17, line 40, delete "claim 1" and insert therefore -- claim 2 --.

Signed and Sealed this

First Day of October, 1996

Attest:

BRUCE LEHMAN

Attesting Officer

Commissioner of Patents and Trademarks